United States Patent [19]

Gray et al.

[11] Patent Number: 5,169,762

[45] Date of Patent: Dec. 8, 1992

[54] HUMAN NERVE GROWTH FACTOR BY RECOMBINANT TECHNOLOGY

[75] Inventors: Alane M. Gray; Axel Ullrich, both of San Francisco, Calif.

[73] Assignee: Genentech, Inc., South San Francisco, Calif.

[21] Appl. No.: 242,093

[22] Filed: Sep. 8, 1988

Related U.S. Application Data

[62] Division of Ser. No. 471,962, Mar. 3, 1983, abandoned.

[51] Int. Cl.$^5$ .................. C12P 21/02; C12N 15/09; C12N 15/70; C12N 1/21
[52] U.S. Cl. .................. 435/69.1; 435/172.3; 435/240.2; 435/252.3; 435/252.33; 435/255; 435/320.1; 530/350; 536/27
[58] Field of Search ............ 435/68, 67, 70, 252.3, 435/320, 69.1, 172.3, 240.2, 252.33, 254, 255, 320.1; 536/27; 530/350

[56] References Cited

U.S. PATENT DOCUMENTS

| | | | |
|---|---|---|---|
| 4,237,224 | 12/1980 | Cohen et al. | 435/91 |
| 4,338,397 | 7/1982 | Gilbert et al. | 435/69.1 |
| 4,358,535 | 11/1982 | Falkow et al. | 435/5 |
| 4,551,433 | 11/1985 | DeBoer | 935/38 |
| 4,704,362 | 11/1987 | Itakura | 435/253 |
| 5,082,093 | 1/1992 | Heinrich et al. | 435/172.3 |

FOREIGN PATENT DOCUMENTS

| | | |
|---|---|---|
| 0002139 | 5/1979 | European Pat. Off. |
| 0036776 | 9/1981 | European Pat. Off. |
| 0093619 | 11/1983 | European Pat. Off. |
| 0432510 | 6/1991 | European Pat. Off. |
| 192827 | 11/1983 | Japan |

OTHER PUBLICATIONS

Moscatelli et al., (1986), Proc. Natl. Acad. Sci., vol. 83, pp. 2091-2095.
Fritsch et al. (1980), "Molecular Cloning and Characterization of the Human β-like Globin Gene Cluster," Cell, vol. 19, pp. 959-972.
Ringold et al. (1981), "Co-Expression of DHFR in CHO cells," J. Mol. Appl. Gen, vol. 1, pp. 165-175.
Subramani et al. (1981), "Expression of Mause DHFR using SV40 Vectors," Mol. Cell Bio, vol. 1, pp. 854-864.
Kaufman et al. (1982), "Amplification and Expression of DHFR," J. Mol. Bio, vol. 159, 601-621.
Williams, Genetic Engineering, vol. 1, 1-55 Academic Press (1981).
Wallace et al., Nuc. Acids Res. 9(4) 879-94 (1981).
Ghosh et al., Methods in Enzymology, 65 580-95 (1980).
Hitzeman et al., Nature, 293:717-722 (1981).
Tuite et al., EMBO J., 1(5):603-608 (1982).
Beach & Norse, Nature, 290:140-142 (1981).
Chang et al., in Genetic Engineering Techniques: Recent Developments, Huang et al., eds., Academic Press (1982) pp. 243-250.
Chater et al., in Current Topics in Microbiology and Immunology, Henle et al., eds., Springer-Verlag (1982) pp. 70-95.
Gray et al., Gene, 32:21-30 (1984).
Bradshaw, Ann. Rev. Biochem., 47:191-216 (1978).
Niall et al., in Biology of Relaxin and its Role in the Human Bigazzi et al., eds., Excerpta Medica, (1983) pp. 32-41.
Valenzvela et al., Nature, 298:347-350 (1982).
Miyanohara et al., PNAS USA, 80:1-5 (1983).
Phaff, Scientific American, Sep. 1981:77-89.
Beck, et al., J. Neurosci. Res. 8:137-152 (1982).
Bigon, et al., Neurochemical Res. 15:1197-1202 (1990).
Dicou, et al., J. Neurosci. Res. 22:13-19 (1989).
Korsching, et al., Proc. Nat. Acad. Sci. 80:3513-3516 (1983).
Rosenthal, et al., Neuron 4:767-773 (1990).
Shelton, et al., Proc. Nat. Acad. Sci. 83:2714-2718 (1986).
Soderstrom, et al., J. Neurosci. Res. 27:665-677 (1990).
Walker, et al., J. Clin. Endocrin. Metab. 53:218-220 (1981).
Warren, et al., Science 210:910-912 (1980).
Ullrich et al., Nature, 303:821-825 (1983).
Maniatis et al., Molecular Cloning: A Laboratory Manual, Cold Spring Harbor Laboratory, NY, 1982.
Itakura et al., Science, 198:1056-1063 (1977).

Kemp & Cowman, PNAS, USA, 78(7):4520–4524 (1981).
Gospodarowicz et al., *Endocrine Rev.*, 8(2):95–114 (1987).
Hsu et al., *Cancer Res.*, 44:4607–4614 (1984).
Sanes, *Nature*, 307:500 (1984).
Yankner and Shooter, *Ann. Rev. Biochem.*, 51:845–868 (1982).
Sutter et al., *J. Biol. Chem.*, 254(13):5972–5982 (1979).
Suda et al., *PNAS, USA*, 75(8):4042–4046 (1978).
Harper et al., *Dev. Biol.*, 77:379–390 (1980).
Harper et al., *Dev. Biol.*, 77:391–402 (1980).
Barde et al., *EMBO J.*, 1(5):549–553 (1982).
Unsicker et al., *PNAS, USA*, 81:2242–2246 (1984).
Leibrock et al., *Nature*, 341:149–152 (1989).
Hohn et al., *Nature*, 344:339–341 (1990).
Maisonpierre et al., *Science*, 247:1446–1451 (1990).
Davies, *TINS*, 11(6):243–244 (1988).
Woods et al., *PNAS, USA*, 79:5661–5665 (1982).
Taniguchi et al., *PNAS, USA*, 77(9):5230–5233 (1980).
Nerve Growth Factors Rush, Ed., John Wiley & Sons, pp. 217–219 (1989).
Breakefield et al., "Cellular and Molecular Biology of Neuronal Development", Black, Ed., Plenum Press, pp. 309–328 (1984).
Harper et al., *J. Biol. Chem.*, 257(14): 8541–8548 (1982).
Bundle A, Bundle of Documents Relating to the Symposium on Cellular and Molecular Biology of Neuronal Development.
"Impacts of Applied Genetics, Micro-Organisms, Plants, and Animals", pub. U.S. Office of Technology Assessment, pp. 61, 67–68, 78 (1981).
Saide et al., *J. Cell. Biol.*, 67:376a (1975).
Old & Primrose, "Principles of Gene Manipulation—An Introduction to Genetic Engineering" (Univ. of Cal. Press, 1981) pp. 28–47 (Ch. 3), 104–120 (Ch. 8), 121–137 (Ch. 9), 157, 160–164.
Goeddel et al., *Nature*, 287:411–416 (1980).
Goeddel et al., *Nucleic Acids Res.*, 8(18):4057–4074 (1980).
Maniatis et al., "Molecular Cloning, A Laboratory Manual", Cold Spring Harbor Laboratory, pp. 224–228, 313, 329, 350, 353, 387–389, 403–433 (Chap. 12).
Goeddel et al., *Nature*, 281:544–548 (1979).
Lawn et al., *Nucl. Acids Res.*, 9(22):6103–6114 (1981).
Pennica et al., *Nature*, 301:214–221 (1983).
Smith et al., *Nucl. Acids Res.*, 10(15):4467–4482 (1982).
Talmadge et al., *PNAS USA*, 77(6):3369–3373 (1980).
Guarente et al., *Cell*, 20:543–553 (1980).
Scott et al., *Nature*, 302:538–540 (1983).
Seeburg et al., *DNA*, 2(1):37–45 (1983).
Miller et al., *J. Biol. Chem.*, 255(16):7521–7524 (1980).
Levi-Montalcini et al., *Cancer Res.*, 14:49–57 (1954).
Rubin & Bradshaw, *J. Neurosc. Res.*, 6:451–464 (1981).
Harper & Thoenen, *J. Neurochem.*, 34(1):5–16 (1980).
Angeletti & Bradshaw, *PNAS USA*, 68(10):2417–2420 (1971).
Yankner & Shooter, *Ann. Rev. Biochem.*, 51:845–868 (1982).
Bevan, *Ind. J. Pharm. Sci*, Jul.–Aug., 1982:65–71 (1982).
Roberts, Promoters: Structure and Functiopn Rodriquez & Chamberlin, eds., Praeger Scientific, New York (1982).
Goldstein et al., *Neurochemical Res.* (3) 175–183 (1978).
Walker et al., *Life Sciences* 26: 195–200 (1980).
Scott et al., *Nature* 302: 538–540 (1983).
Catanazaro et al., "Manipulation and Expression of Genes in Eukaryotes" (Nagley et al., eds.) Academic Press, 11–12 (1983).
Hogue-Angeletti et al., *Biochemistry* 15: 26–34 (1976).
Hogue-Angeletti et al., *Biochemistry* 12: 100–115 (1973).
Harper et al., *J. Biol. Chem.* 257: 8541–8548 (1982).
Ben-Bassat et al., *J. Bacteriology* 169: 751–757 (1987).
Mobley et al., *Biochemistry* 15: 5543–5552 (1976).
Riemschneider, *Z. Naturforsch*, 37C:1045–1047 (1982)—English translation.
Ullrich et al., "Cellular and Molecular Biology of Neuronal Development", Black ed., Plenum Press, pp. 293–307 (1984).

*Primary Examiner*—Richard A. Schwartz
*Assistant Examiner*—Richard M. Lebovitz
*Attorney, Agent, or Firm*—Max D. Hensley

[57] ABSTRACT

The β-subunit of human nerve growth factor (βNGF) is prepared in essentially pure form in commercially viable quantities using recombinant DNA technology. The nucleotide sequence and vectors encoding human βNGF and host cells transformed with the vectors are also provided.

17 Claims, 14 Drawing Sheets

MOUSE βNGF SEQUENCES

```
      1                                                    10
      Ser  Ser  Thr  His  Pro  Val  Phe  His  Met  Gly  Glu  Phe  Ser  Val  Cys
      TCG  TCG  ACG  CAT  CCG  GTG  TTT  CAT  ATG  GGG  GAA  TTT  TCG  GTG  TGT
5'     A    A    A    C    A    A    C    C         A    G    C    A    A    C
      AGT  AGT  T         T    T                    T              AGT  T
       C    C   C         C    C                    C               C   C

20
      Asp  Ser  Val  Ser  Val  Trp  Val  Gly  Asp  Lys  Thr  Thr  Ala  Thr  Asn
      GAT  TCG  GTG  TCG  GTG  TGG  GTG  GGG  GAT  AAA  ACG  ACG  GCG  ACG  AAT
       C    A    A    A    A         A    A    C    G    A    A    A    A    C
           AGT       AGT                                 T    T    T    T
            C         C                                  C    C    C    C
                 30
                                         40
      Ile  Lys  Gly  Lys  Glu  Val  Thr  Val  Leu  Ala  Glu  Val  Asn  Ile  Asn
      ATT  AAA  GGG  AAA  GAA  GTG  ACG  GTG  CTG  GCG  GAA  GTG  AAT  ATT  AAT
       C    G    A    G    G    A    A    A    T    A    G    A    C    C    C
       A         T                   T    T    T    T         T         A
                 C                   C    C    C    C         C 50                                                    60
      Asn  Ser  Val  Phe  Arg  Gln  Tyr  Phe  Phe  Glu  Thr  Lys  Cys  Arg  Ala
      AAT  TCG  GTG  TTT  CGG  CTA  TAT  TTT  TTT  GAA  ACG  AAA  TGT  CGG  GCG
       C    A    A    C    A    G    C    C    C    G    A    G    C    A    A
           AGT  T         T                                  T         T    T
            C   C         C                                  C         C    C
```

```
        3'  ATA  AAA  AAA  CTT  TG  5'
   3         G    G    G    C
                  16 x 14
```

Fig. 1A.

```
                                              70
Ser Asn Pro Val Glu Ser Gly Cys Arg Gly Ile Asp Ser Lys His
TCG AAT CCG GTG GAG TCG GGG TGT CGG GGG ATT GAT TCG AAA CAT
 A   C   A   A   A   A       C   A   A   C   A   A   G   C
AGT     T   T       AGT         T       T       AGT
 C      C   C        C          C       C        C 2  3' TTT GTA
                                                        C   G
                                                        8 x 12

80
Trp Asn Ser Tyr Cys Thr Thr Thr His Thr Phe Val Lys Ala Leu      90
TGG AAT TCG TAT TGT ACG ACG ACG CAT ACG TTT GTG AAA GCG CTG
     C   A   C   C   A   A   A   C   A   C   A   G   A   T
        AGT             T   T   T   T       T       T   T
         C              C   C   C   .C      C       C   C

ACC TTA 5'
     G
8 x 12
Thr Thr Asp Glu Lys Gln Ala Ala Tyr Arg Phe Ile Arg Ile Asn
ACG ACG GAT GAA AAA CAA GCG GCG TAT CGG TTT ATT CGG ATT AAT
 A   A   C   G   G   G   A   A   C   A   C   C   A   C   C
 T   T           T                   T       A   T   A
 C   C           C                   C       C

3' CTA CTT TTT GTT CG 5'
1      G   C   C   C
       16 x 14

110                           118
Thr Ala Cys Val Cys Val Leu Ser Arg Lys Ala Thr Arg
ACG GCG TGT GTG TGT GTG CTG TCG CGG AAA GCG ACG CGG                  3'
 A   A   C   A   C   A   T   A   A   G   A   A   A
 T   T       T       T   T  AGT  T       T   T   T
 C   C       C       C   C   C   C       C   C   C
```

Fig. IB.

```
AGCGCATCGAGTGACTTTGGAGCTGGCCTTATATTTGGATCTCCCGGGCAGCTTTTTGG
1         10        20        30        40        50
```

```
                         -187                              -180
                         met  leu cys leu lys pro val lys leu gly ser
AAACTCCTAGTGAAC          ATG  CTG TGC CTC AAG CCA GTG AAA TTA GGC TCC
60         70                 80              90              100
```

```
                                    -170
leu glu val gly his gly gln his gly gly val leu ala cys gly
CTG GAG GTG GGA CAC GGG CAG CAT GGT GGA GTT TTG GCC TGT GGT
        110         120         130         140         150
```

```
       -160                                         -150
arg ala val gln gly ala gly trp his ala gly pro lys leu thr
CGT GCA GTC CAG GGG GCT GGA TGG CAT GCT GGA CCC AAG CTC ACC
            160         170         180         190
```

```
                         -140
ser val ser gly pro asn lys gly phe ala lys asp ala ala phe
TCA GTG TCT GGG CCC AAT AAA GGT TTT GCC AAG GAC GCA GCT TTC
        200         210         220         230         240
```

```
       -130                                  -120
tyr thr gly arg ser glu val his ser val met ser met leu phe
TAT ACT GGC CGC AGT GAG GTG CAT AGC GTA ATG TCC ATG TTG TTC
            250         260         270         280
```

```
                    -110
tyr thr leu ile thr ala phe leu ile gly val gln ala glu pro
TAC ACT CTG ATC ACT GCG TTT TTG ATC GGC GTA CAG GCA GAA CCG
        290         300         310         320         330
```

```
       -100                                  -90
tyr thr asp ser asn val pro glu gly asp ser val pro glu ala
TAC ACA GAT AGC AAT GTC CCA GAA GGA GAC TCT GTC CCT GAA GCC
            340         350         360         370
```

```
                         -80
his trp thr lys leu gln his ser leu asp thr ala leu arg arg
CAC TGG ACT AAA CTT CAG CAT TCC CTT GAC ACA GCC CTC CGC AGA
        380         390         400         410         420
```

```
       -70                                   -60
ala arg ser ala pro thr ala pro ile ala ala arg val thr gly
GCC CGC AGT GCC CCT ACT GCA CCA ATA GCT GCC CGA GTG ACA GGG
            430         440         450         460
```

```
                              -50
gln thr arg asn ile thr val asp pro arg leu phe lys lys arg
CAG ACC CGC AAC ATC ACT GTA GAC CCC AGA CTG TTT AAG AAA CGG
        470         480         490         500         510
```

```
     -40                                      -30
arg leu his ser pro arg val leu phe ser thr gln pro pro pro
AGA CTC CAC TCA CCC CGT GTG CTG TTC AGC ACC CAG CCT CCA CCC
            520         530         540         550
```

*Fig. 4A.*

```
                                           -20
     thr ser ser asp thr leu asp leu asp phe gln ala his gly thr
     ACC TCT TCA GAC ACT CTG GAT CTA GAC TTC CAG GCC CAT GGT ACA
        560         570         580         590         600

-10       ////////                                     1
     ile pro phe asn arg thr his arg ser lys arg ser ser thr his
     ATC CCT TTC AAC AGG ACT CAC CGG AGC AAG CGC TCA TCC ACC CAC
                610         620         630         640

10
     pro val phe his met gly glu phe ser val cys asp ser val ser
     CCA GTC TTC CAC ATG GGG GAG TTC TCA GTG TGT GAC AGT GTC AGT
        650         660         670         680         690

20                                   30
     val trp val gly asp lys thr thr ala thr asp ile lys gly lys
     GTG TGG GTT GGA GAT AAG ACC ACA GCC ACA GAC ATC AAG GGC AAG
                700         710         720         730

40                         ////////
     glu val thr val leu ala glu val asn ile asn asn ser val phe
     GAG GTG ACA GTG CTG GCC GAG GTG AAC ATT AAC AAC AGT GTA TTC
        740         750         760         770         780

50                                   60
     arg gln tyr phe phe glu thr lys cys arg ala ser asn pro val
     AGA CAG TAC TTT TTT GAG ACC AAG TGC CGA GCC TCC AAT CCT GTT
                790         800         810         820

70
     glu ser gly cys arg gly ile asp ser lys his trp asn ser tyr
     GAG AGT GGG TGC CGG GGC ATC GAC TCC AAA CAC TGG AAC TCA TAC
        830         840         850         860         870

80                                   90
     cys thr thr thr his thr phe val lys ala leu thr thr asp glu
     TGC ACC ACG ACT CAC ACC TTC GTC AAG GCG TTG ACA ACA GAT GAG
                880         890         900         910

100
     lys gln ala ala trp arg phe ile arg ile asp thr ala cys val
     AAG CAG GCT GCT TGG AGG TTC ATC CGG ATA GAC ACA GCC TGT GTG
        920         930         940         950         960

110                             ■■■■■■■
     cys val leu ser arg lys ala thr arg arg gly OP
     TGT GTG CTC AGC AGG AAG GCT ACA AGA AGA GGC TGA CTTGCCTGCAGC
                970         980         990        1000        1010
     CCCCTTCCCCACCTGCCCCCTCCACATCTCCTGGGCCCCTCCCTACCTCAGCCTGTAAATTA
            1020        1030        1040        1050        1060        1070
     TTTTAAATTATAAGGACTGCATGATAATTTATCGTTTATACAATTTTAAAGACATTA
            1080        1090        1100        1110        1120        1130
     TTTATTAAATTTTCAAAGCATCCTGTATACCGAA
            1140        .1150        1160
```

```
AGCGCATCGAGTGACTTTGGAGCTGGCCTTATATTTGGATCTCCCGGGCAGCTTTTTGGA
```

```
                    -187                              -180
                    met leu cys leu lys pro val lys leu gly ser
AACTCCTAGTGAAC      ATG CTG TGC CTC AAG CCA GTG AAA TTA GGC TCC   m
                    ___ ___ ___ ___ ___ ___ ___ ___ ___ ___ ___   h
                                    -170
leu glu val gly his gly gln his gly gly val leu ala cys  gly
CTG GAG GTG GGA CAC GGG CAG CAT GGT GGA GTT TTG GCC TGT  GGT
___ ___ ___ ___ ___ ___ ___ ___ ___ ___ ___ ___ ___  A
                                            ↑          ser
                                           IVS  -150
 -160
arg ala val gln gly ala gly trp his ala gly pro lys leu thr
CGT GCA GTC CAG GGG GCT GGA TGG CAT GCT GGA CCC AAG CTC ACC   m
         A                                              G
                                                        ser   h -140
ser val ser gly pro asn lys gly phe ala lys asp ala ala phe
TCA GTG TCT GGG CCC AAT AAA GGT TTT GCC AAG GAC GCA GCT TTC
    C                C A     C   A   A      GA
    ala              asn ser     thr        gly -130                                   -120
tyr thr gly arg ser glu val his ser val met ser met leu phe
TAT ACT GGC CGC AGT GAG GTG CAT AGC GTA ATG TCC ATG TTG TTC   m
    C       A   C                                              h
    pro     his thr  ↑
                    IVS
                                -110
tyr thr leu ile thr ala phe leu ile gly val gln ala glu pro
TAC ACT CTG ATC ACT GCG TTT TTG ATC GGC GTA CAG GCA GAA CCG
                    A   T   C           A       G          A
                                        ile -100                                         -90
tyr thr asp ser asn val pro glu gly asp ser val pro glu ala
TAC ACA GAT AGC AAT GTC CCA GAA GGA GAC TCT GTC CCT GAA GCC   m
    C   T       G            C      C   A   A   C   C   T    h
    his ser glu             ala     his thr ile     gln val -80
his trp thr lys leu gln his ser leu asp thr ala leu arg arg
CAC TGG ACT AAA CTT CAG CAT TCC CTT GAC ACA GCC CTC CGC AGA
                                        T       T -70                                   -60
ala arg ser ala pro thr ala pro ile ala ala arg val thr gly
GCC CGC AGT GCC CCT ACT GCA CCA ATA GCT GCC CGA GTG ACA GGG   m
                C       G A      G G          A    C    G G
                        ala      ala                    ala -50
gln thr arg asn ile thr val asp pro arg leu phe lys lys arg
CAG ACC CGC AAC ATC ACT GTA GAC CCC AGA CTG TTT AAG AAA CGG
                T       G            G               A   G -40                                         -30
arg leu his ser pro arg val leu phe ser thr gln pro pro pro
AGA CTC CAC TCA CCC CGT GTG CTG TTC AGC ACC CAG CCT CCA CCC   m
C       GT                              T                GT   h
        arg                                              arg
```

*Fig. 6A.*

```
       thr  ser  ser  asp  thr  leu  asp  leu  asp  phe  gln  ala  his  gly  thr
       ACC  TCT  TCA  GAC  ACT  CTG  GAT  CTA  GAC  TTC  CAG  GCC  CAT  GGT  ACA
       GAA  G    G              A              G              G    T    GG       G T
       glu  ala  ala            gln                           glu  val  gly      ala -10              ▨▨▨▨▨                                    ┌─ 1 ────────────┐
       ile  pro  phe  asn  arg  thr  his  arg  ser  lys  arg │ ser  ser  thr  his │ m
       ATC  CCT  TTC  AAC  AGG  ACT  CAC  CGG  AGC  AAG  CGC │ TCA  TCC  ACC  CAC │ h
       GC   C                        A                    G │                A  T │
       ala                                                   │              ser   │
┌──────┘                                                      └─ ─ ─ ─ ─ ─ ─ ─ ─ ─
│ pro  val  phe  his  met  gly  glu  phe  ser  val  cys  asp  ser  val  ser │
│ CCA  GTC  TTC  CAC  ATG  GGG  GAG  TTC  TCA  GTG  TGT  GAC  AGT  GTC  AGT │
│   C  A              G           C    A              G                   C │
│      ile            arg                                                    │
│
│ 20                                       30
│ val  trp  val  gly  asp  lys  thr  thr  ala  thr  asp  ile  lys  gly  lys │ m
│ GTG  TGG  GTT  GGA  GAT  AAG  ACC  ACA  GCC  ACA  GAC  ATC  AAG  GGC  AAG │ h
│                G                        C                                  │
│
│                                40                        ▨▨▨▨▨
│ glu  val  thr  val  leu  ala  glu  val  asn  ile  asn  asn  ser  val  phe │
│ GAG  GTG  ACA  GTG  CTG  GCC  GAG  GTG  AAC  ATT  AAC  AAC  AGT  GTA  TTC │
│           TG        T    GA                                                │
│           met            gly                                               │
│
│ 50                                                 60
│ arg  gln  tyr  phe  phe  glu  thr  lys  cys  arg  ala  ser  asn  pro  val │
│ AGA  CAG  TAC  TTT  TTT  GAG  ACC  AAG  TGC  CGA  GCC  TCC  AAT  CCT  GTT │ m
│  A                                             G   A    C              C  │ h
│ lys                                              asp  pro
```

*Fig. 6B.*

```
                        70
 glu ser gly cys arg gly ile asp ser lys his trp asn ser tyr
 GAG AGT GGG TGC CGG GGC ATC GAC TCC AAA CAC TGG AAC TCA TAC
  C   C                   T       A   G                   T
 asp 80
 cys thr thr thr his thr phe val lys ala leu thr thr  asp glu
 TGC ACC ACG ACT CAC ACC TTC GTC AAG GCG TTG ACA ACA  GAT GAG    m
  T                       T                   C  TG       GC    h
                                                 met       gly 100
 lys gln ala ala trp arg phe ile arg ile asp thr ala cys val
 AAG CAG GCT GCT TGG AGG TTC ATC CGG ATA GAC ACA GCC TGT GTG
              C       C   T               T   G 110
 cys val leu ser arg lys ala thr arg arg gly OP
 TGT GTG CTC AGC AGG AAG GCT ACA AGA AGA GGC TGA CTTGCCTGCAGC    m
                             GTG         C      CCTGCCGACACG    h
                             val         ala
```

CCCCTTCCCCACCTGCCCCCTCCACACTCTCCTGGGCCCCTCCCTACCTCAGCCTGTAAA    m
CTCCCTCCCCCTGCCCCTTCTACACTCTCCTGGGCCCCTCCCTACCTCAACCTGTAAATT    h

TTATTTTAAATTATAAGGACTGCATGATAATTTATCGTTTATACAATTTTAAAGACATTA    m
ATTTTAAATTATAAGGACTGCATGGTAATTTATAGTTTATACAGTTTTAAAGAATCATTA    h

TTTATTAAATTTTCAAAGCATCCTGTATACCGAA                              m
TTTATTAAATTTTTGGAAGCATCCTGTGTGCTGA                              h

*Fig. 6C*

Human βNGF Expresssion

```
                                                EcoRI
         XbaI        I              II              MetSerSerHisProIlePheSerValCysAspValGluArgGlyAspLysThrThrAlaT
                                                    ATGTCATCGAGTCATCCAATCTTCCACAGGGGCGAATTCTCAGTGTGTGACAGTGTCAGCGGTGGGTTGGGATAAGACCACCGCCA
         CTAGAATT                                   TACAGTAGCTCAGTAGGTTAGAAGGTGTCCCCGCTTAAGAGTCACACACTGTCACAGTCGCACCCAACCCTATTCTGGTGGCGGT
             TTAA                                                                 IV
                                             III hrAspIleLysGlyLysGluValMetValLeuGlyGluValAsnIleAsnAsnSerValPheLysGlnTyrPhePheGluThrLysCysArgAspProAs
         CAGACATCAAGGGCAAGGAGGTGATGGTGTTGGGAGAGGTGAACATTAACAACAGTGTATTCAAACAGTACTTTTTTGAGACCAAGTGCCGGGACCCAAA
         GTCTGTAGTTCCCGTTCCTCCACTACCACAACCCTCTCCACTTGTAATTGTTGTCACATAAGTTTGTCATGAAAAAACTCTGGTTCACGGCCCTGGGTTT nProValAspSerGlyCysArgGlyIleAspSerLysHisTrpAsnSerTyrCysThrThrThrHisThrPheValLysAlaAlaLeuThrMetAspGlyLys
         TCCCGTTGACAGCGGCTGCCGGGGTATTGACTCCAAGCACTGGAACTCATATTGTACCACGACTCACACCTTTGTCAAGGCGCTGACCATGGATGGCAAG
         AGGGCAACTGTCGCCGACGGCCCCATAACTGAGGTTCGTGACCTTGAGTATAACATGGTGCTGAGTGTGAAACAGTTCCGCGACTGGTACCTACCGTTC

GlnAlaAlaTrpArgPheIleArgIleAspThrAlaCysValCysValLeuSerArgLysAlaValArgEnd
         CAGGCTGCCTGGCGGTTTATCCGGATAGATACGGCCTGTGTGTGTGCTCAGCAGGAAGGCTGTGAGATAGTGAC
         GTCCGACGGACCGCCAAATAGGCCTATCTATGCCGGACACACACACGAGTCGTCCTTCCGACACTCTATCAGCTG
                                HgjAI                         V
                                                               VI
```

Fig. 7.

HUMAN NERVE GROWTH FACTOR BY RECOMBINANT TECHNOLOGY

This application is a divisional application of application Ser. No. 06/471,962, filed Mar. 3, 1983, now abandoned.

FIELD OF THE INVENTION

This invention relates to the polypeptide hormone human Nerve Growth Factor (NGF), its preparation using recombinant technology and compositions which contain it.

BACKGROUND OF THE INVENTION

A. Nerve Growth Factor

A multi-component protein of molecular weight ~130,000 has been isolated from mouse salivary glands, it being particularly concentrated in the glands of male mice, which is commonly referred to as "Nerve Growth Factor." The principal neural activity exhibited by the protein has been its ability to cause an increase in the size of sensory neurons, nerve cells which transmit impulses from sensory receptors to the brain, and in the size of sympathetic neurons, one of the two kinds of neurons which make up the autonomic nervous system which regulates the functional activity of the circulatory system, the glands, smooth muscles and other organs.

NGF as obtained by extraction at neutral pH from mouse salivary glands is known as 7S NGF and is made up of three subunits termed $\alpha$-, $\beta$-, and $\gamma$-subunits. All of the neural activity of 7S NGF is exhibited by the $\beta$-subunit, a dimer of two identical 118 amino acid peptides bound together by non covalent forces. This subunit is also referred to as 2.5S NGF. The $\alpha$-subunit has no known biological activity. The $\gamma$-subunit, however, is an arginine esteropeptidase. The initial genetic product in the synthesis of NGF is a prepro-NGF polypeptide which is cleaved by the $\gamma$-subunit. The $\gamma$-subunit has also been shown to accelerate wound healing in mice.

Recently, a third NGF component (M. wt. ~116,000) has been reported to have been isolated from mouse salivary glands and to have shown to exhibit the property of being a plasminogen activator, i.e., it converts plasminogen to plasmin, suggesting its utility in the lysis of blood clots. See European Patent Application "Nerve Growth Factor and Process For Obtaining It" 78300656.2 (Publication No. 0002139A1) filed Nov. 22, 1978, published May 30, 1979.

As indicated above, the neural activity of NGF is exhibited by the $\beta$-subunit (hereinafter $\beta$NGF). It has been shown to stimulate markedly regenerative resprouting of transected axons of central adrenergic neurons, a property which makes it useful in the repair of damaged axons.

B. Recombinant DNA Technology

Recombinant DNA technology has reached the age of some sophistication. Molecular biologists are able to recombine various DNA sequences with some facility, creating new DNA entities capable of producing copious amounts of exogenous protein product in transformed microbes and cell cultures. The general means and methods are in hand for the in vitro ligation of various blunt ended or "sticky" ended fragments of DNA, producing potent expression vectors useful in transforming particular organisms, thus directing their efficient synthesis of desired exogenous product. However, on an individual product basis, the pathway remains tortuous and the science has not advanced to a stage where regular predictions of success can be made. Indeed, those who portend successful results without the underlying experimental basis, do so at considerable risk of inoperability.

DNA recombination of the essential elements, i.e., an origin of replication one or more phenotypic selection characteristics, an expression promoter, heterologous gene insert and remainder vector, generally is performed outside the host cell. The resulting recombinant replicable expression vector, or plasmid, is introduced into cells by transformation and large quantities of the recombinant vehicle are obtained by growing the transformant. Where the gene is properly inserted with reference to portions which govern the transcription and translation of the encoded DNA message, the resulting expression vector is useful to produce the polypeptide sequence for which the inserted gene codes, a process referred to as "expression." The resulting product may be obtained by lysis, if necessary, of the host cell and recovery of the product by appropriate purifications from other proteins.

In practice, the use of recombinant DNA technology can express entirely heterologous polypeptides—so-called direct expression—or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment.

Similarly, the art of cell or tissue cultures for studying genetics and cell physiology is well established. Means and methods are in hand for maintaining permanent cell lines, prepared by successive serial transfers from isolated normal cells. For use in research, such cell lines are maintained on a solid support in liquid medium, or by growth in suspension containing support nutriments. Scale-up for large preparations seems to pose only mechanical problems.

Likewise, protein biochemistry is a useful, indeed necessary, adjunct in biotechnology. Cells producing the desired protein also produce hundreds of other proteins, endogenous products of the cell's metabolism. These contaminating proteins, as well as other compounds, if not removed from the desired protein, could prove toxic if administered to an animal or human in the course of therapeutic treatment with desired protein. Hence, the techniques of protein biochemistry come to bear, allowing the design of separation procedures suitable for the particular system under consideration and providing a homogeneous product safe for intended use. Protein biochemistry also proves the identity of the desired product, characterizing it and ensuring that the cells have produced it faithfully with no alterations or mutations. This branch of science is also involved in the design of bioassays, stability studies and other procedures necessary to apply before successful clinical studies and marketing can take place.

SUMMARY OF THE INVENTION

The present invention provides the $\beta$-subunit of human NGF, which previously had not been isolated by extraction techniques or otherwise synthesized, in essentially pure form. Further, we have discovered that, unexpectedly, $\beta$-NGF can be expressed as a heterologous protein in *E. Coli* as a mature polypeptide, i.e., free of any fused homologous protein which might be required to afford it protection from cellular enzymes which recognize it as foreign protein. We believe the β-subunit of NGF to be the smallest protein directly expressed as mature protein in *E. coli*.

The β-NGF which the invention provides is useful in treating nerve damage or for other related purposes for which it is beneficial. Being identical with naturally secreted human β-NGF, but free of other protein of mammalian origin, it is unlikely its use will result in an immunogenic response during treatment with it, unlike the case when peptide hormones of non-human origin are used to treat human illness. Furthermore, being obtained as a heterologous protein, the β-NGF will be essentially free of other proteins of mammalian origin which accompany β-NGF obtained as a tissue extract and which may exhibit undesirable biological activity in compositions which contain them.

The invention is further directed to replicable DNA expression vectors which contain a gene sequence which codes for the polypeptide in expressible form. The invention is also directed to recombinant host cells such as microorganism strains or cell lines transformed with such vectors, and to the cultures thereof. Still further, the invention is directed to compositions comprising the polypeptide for parenteral administration.

Accordingly an object of this invention is to acquire human β-NGF essentially free of other mammalian proteins.

Another object is to obtain human β-NGF in quantities in excess of those which are possible by extraction from natural sources.

BRIEF DESCRIPTION OF THE DRAWINGS

FIG. 1 shows the amino acid sequence of the β-subunit of mouse NGF and gene sequences coding for it and the complementary DNA strands for specific segments of the gene.

FIG. 4 shows the physical map of the recombinant phage λhN8 and flanking regions in the human genome.

FIG. 5 is the nucleotide sequence of the human βNGF chromosomal gene.

FIG. 6 shows a comparison of nucleotide sequences of human and mouse Prepro- βNGF gene and amino acid sequences.

FIG. 7 shows the gene constructed for expression of human βNGF.

DETAILED DESCRIPTION

Host Cell Cultures and Vectors

Figure 2:
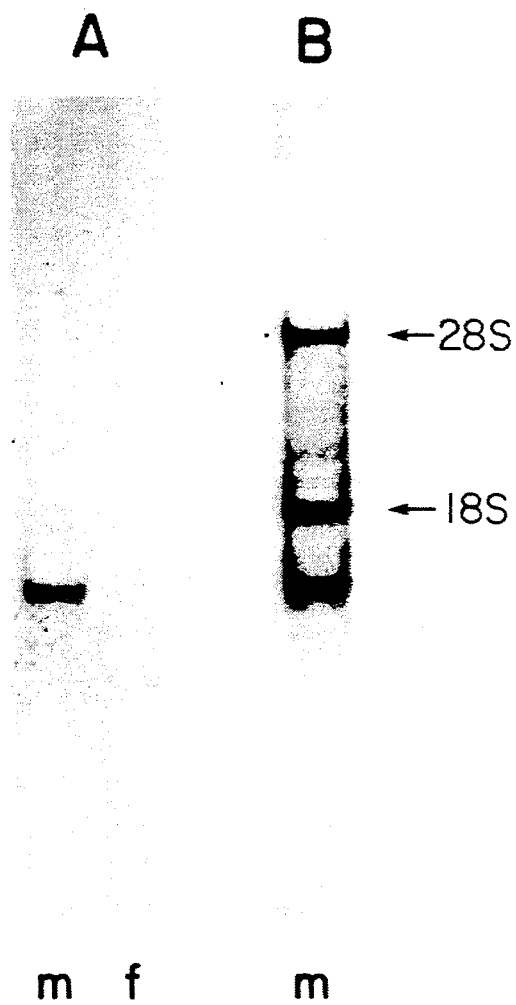
FIG. 2 shows a Northern Blot Analysis of clones containing segments of βNGF mRNA.

As used in the present application, the term "expression vector" includes vectors which are capable of expressing DNA sequences contained therein, where such sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition, and any DNA sequence which is capable of effecting expression of a specified DNA code disposed therein is included in this term as it is applied to the specified sequence. In general, expression vectors of utility in recombinant DNA techniques are often in the form of "plasmids" which refer to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Further as used herein, the term "recombinant host cells" refers to cells which have been transformed with vectors constructed using recombinant DNA techniques.

The vectors and methods disclosed herein are suitable for use in host cells over a wide range of prokaryotic and eukaryotic organisms.

In general, of course, prokaryotes are preferred for cloning of DNA sequences in constructing the vectors useful in the invention. For example, *E. coli* K12 strain 294 (ATTC No. 31446) is particularly useful. Other microbial strains which may be used include *E. coli* strains such as *E. coli* B, and *E. coli* X1776 (ATTC No. 31537). These examples are, of course, intended to be illustrative rather than limiting.

Prokaryotes may also be used for expression. The aforementioned strains, as well as *E. coli* W3110 (F-, λ-, prototrophic, ATTC No. 27325), bacilli such as *Bacillus subtilus,* and other enterobacteriaceae such as *Salmonella typhimurium* or *Serratia marcescens,* and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (Bolivar, et al., *Gene* 2:95 (1977)). pBR322 contains genes for ampicillin and tetracycline resistance and thus provides easy means for identifying transformed cells. The pBR322 plasmid, or other microbial plasmid, must also contain, or be modified to contain, promoters which can be used by the microbial organism for expression of its own proteins. Those promoters most commonly used in recombinant DNA construction include the β-lactamase (penicillinase) and lactose promoter systems (Chang et al, *Nature,* 275:615 (1978); Itakura, et al., *Science,* 198: 1056 (1977); Goeddel, et al, *Nature,*281: 544 (1979)) and a tryptophan (trp) promoter system (Goeddel, et al, *Nucleic Acids Res.,* 8: 4057 (1980); EPO Appl. Publ. No.. 0036776). While these are the most commonly used, other microbial promoters have been discovered and utilized, and details concerning their nucleotide sequences have been published, enabling a skilled worker to ligate them functionally with plasmid vectors (Siebenlist, et al, *Cell* 20: 269 (1980)).

In addition to prokaryotes, eukaryotic microbes, such as yeast cultures, may also be used. *Saccharomyces cere-* visiae, or common baker's yeast, is the most commonly used among eukaryotic microorganisms, although a number of other strains are commonly available. For expression in *Saccharomyces*, the plasmid YRp7, for example, (Stinchcomb, et al, *Nature*, 282: 39 (1979); Kingsman, et al, *Gene*, 7: 141 (1979); Tschemper, et al, *Gene*, 10: 157 (1980)) is commonly used. This plasmid already contains the trpl gene which provides a selection marker for a mutant strain of yeast lacking the ability to grow in tryptophan, for example ATCC No. 44076 or PEP4-1 (Jones, *Genetics*, 85: 12 (1977)). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., *J. Biol. Chem.*, 255: 2073 (1980)) or other glycolytic enzymes (Hess, et al, *J. Adv. Enzyme Reg.*, 7: 149 (1968); Holland, et al, *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences. It will be understood that this invention, although described herein in terms of a preferred embodiment, should not be construed as limited to those sequences exemplified.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, *Nature*, 273: 113 (1978) incorporated herein by reference). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

Methods Employed

If cells without formidable cell wall barriers are used as host cells, transfection is carried out by the calcium phosphate precipitation method as described by Graham and Van der Eb, *Virology*, 52: 546 (1978). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F.N., et al, *Proc. Natl. Acad. Sci.* (USA), 69: 2110 (1972).

Construction of suitable vectors containing the desired coding and control sequences employs standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 $\mu$g plasmid or DNA fragments is used with about 1 unit of enzyme in about 20$\mu$l of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° with 10 units of *E. coli* DNA Polymerase I (Klenow), phenol-chloroform extracted, and ethanol precipitated.

Size separation of the cleaved fragments is performed using 6 percent polyacrylamide gel described by Goeddel, D., et al, *Nucleic Acids Res.*, 8: 4057 (1980), incorporated herein by reference.

For ligation, approximately equimolar amounts of the desired components, suitably end tailored to provide correct matching, are treated with about 10 units T4 DNA ligase per 0.5 $\mu$g DNA. (When cleaved vectors are used as components, it may be useful to prevent religation of the cleaved vector by pretreatment with bacterial alkaline phosphatase.)

The ligation mixture was used to transform *E. coli* K12 strain 294 (ATLC 31446), and successful transformants were selected by ampicillin resistance. Plasmids from the transformants were prepared, analyzed by restriction and/or sequenced by the method of Messing, et al, *Nucleic Acids Res.*, 9: 309 (1981) or by the method of Maxam, et al, *Methods in Enzymology*, 65: 499 (1980).

Preferred Embodiments

The following description of preferred embodiments involving polypeptide expression in *E. coli* is intended to illustrate but not to limit the invention.

Isolation of cDNA clones coding for mouse pro-βNGF

In order to obtain a gene coding for the β-subunit of human NGF, it was determined to use cloned cDNA coding for mouse βNGF as a hybridization probe.

The cDNA cloning approach took advantage of the known amino acid sequence of the mouse βNGF subunit which is shown in FIG. 1, employing synthetic oligonucleotide primers; the difference in NGF levels found in male and female mouse salivary glands was used as an additional means of identification. Three small portions of the mouse βNGF amino acid sequence were chosen, and oligonucleotide pools complementary to all possible sequences coding for them were synthesized by the method of Crea, et al, *Nucleic Acids Res.*, 8: 2331 (1980). The nucleotide sequences for the coding and complementary strands are shown in FIG. 1.

Initial attempts to identify or isolate mouse βNGF cDNA clones from an oligo dT-primed, cDNA bank from male mouse salivary glands failed, using the synthetic oligonucleotides as hybridization probes. This result indicated that while βNGF comprised 0.1 percent of the protein in the male salivary glands, its mRNA was not of equal abundance. Therefore, the primer pool representing sequences closest to the carboxyl terminus of the protein (FIG. 1, 1) was used to specifically prime reverse transcription of polyA-containing (A+) RNA, from male salivary glands, in order to first enrich for βNGF-specific nucleotide sequences. Molecules of cDNA greater than 200 bp in length were cloned into the well known plasmid pBR322. A total of 10,000 clones was screened using the 5'-$^{32}$P-labeled NGF primer pool originally used in the cDNA priming as a hybridization probe and 0.8 percent of the clones gave a positive signal under high stringency hybridization conditions. It is likely that the remaining 99.2 percent of the "primed" cDNA bank resulted from self-priming as well as from priming by trace amounts of oligo dT eluted during preparation of polyA+ MSG RNA. S1 nuclease treatment during the cloning procedure may also have damaged some of the terminal primer sequence, resulting in fewer detected positive clones.

Clones scored as positive in the first screen were rescreened using radiolabeled primer pools 2 and 3 derived from DNA sequences upstream from oligonucleotide pool 1 as shown in FIG. 1, as hybridization probes. In addition, $^{32}$P-cDNA primed with pool 1 from polyA+ RNA from either male or female mouse salivary glands were used as probes on duplicate filters. A total of 10 male-specific clones, again in pBR322, which hybridized with oligonucleotide pools 2 and 3 were identified. Restriction enzyme analyses demonstrated that all 10 had common HaeIII and HinfI fragments. The clone containing a plasmid which we designated pmβN-9G1 and which expressed the longest DNA insert (~700 bp) was sequenced in its entirety. The amino acid sequence deduced from the nucleotide sequence contained the expected NGF sequence in one translational frame in addition to an NH$_2$-terminal prosequence. See FIG. 4. Further details of the construction and identification of bacterial clones containing mouse NGF cDNA sequences are given hereinafter.

Figure 3:
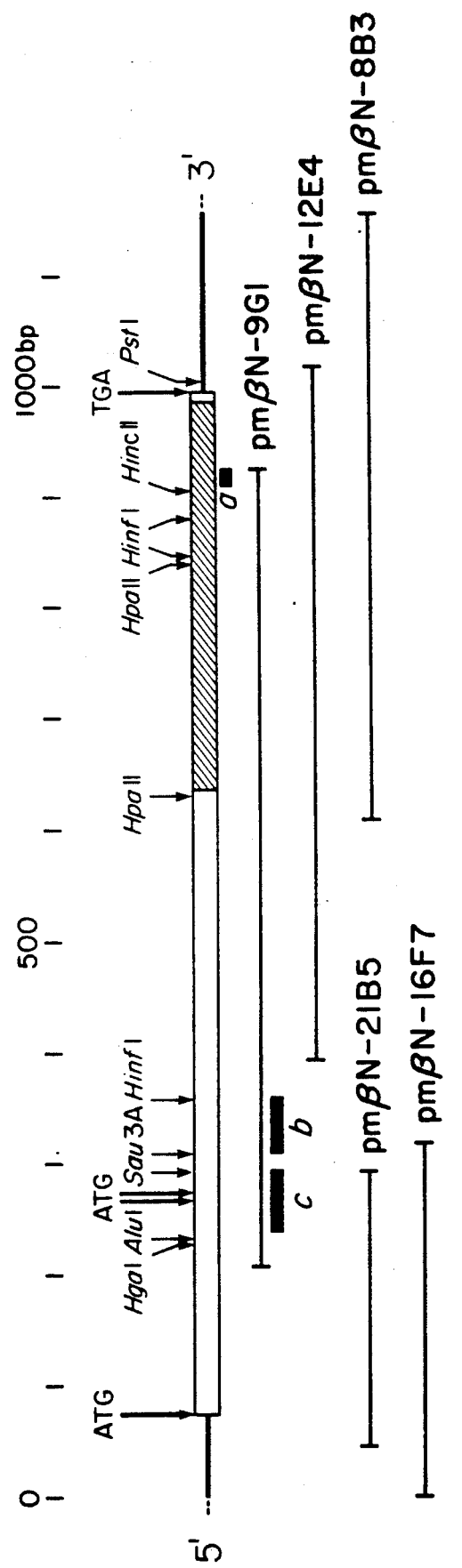
FIG. 3 is a partial restriction map of the mouse NGF gene and the approximate correspondence between the nucleotide sequences of plasmids constructed in the making of the invention with the nucleotide sequence of the mouse NGF gene.

In order to determine the size of the complete NGF mRNA, northern blot hybridization as well as primer extension analysis was employed. A 470 bp long $^{32}$P-labeled DNA fragment (RsaI-RsaI 789, FIG. 3) that included NGF as well as propeptide sequences hybridized to an RNA species about 1300 nucleotides long which was male mouse salivary gland specific. A primer extension experiment using 2 short, double stranded, 5' end-labeled restriction fragments (see legend, FIG. 3) localized the 5' end of the βNGF mRNA to about 230 bases upstream from the 5' end of the pmβN-9G1 cDNA fragment, leaving approximately 370 bases downstream from the 3' end of our clone. All but ~30 nucleotides of the missing 5' sequences are contained in clones we designated pmβN-16F7 and pmβN-21B5, which overlap each other and clone pmβN-9G1 as shown in FIG. 3 and which were isolated as described in the more detailed discussion hereinafter concerning the use of restriction fragments to prime cDNA synthesis.

In order to obtain cloned cDNA which included the sequences from the 3' end of the primer sequence downstream to the 3' polyA sequence, we first enriched for βNGF mRNA by fractionating total polyA+ male mouse salivary gland RNA on a preparative urea agarose gel. The largest size fraction, containing sequences hybridizing to a βNGF cDNA probe, was used for oligo dT-primed cDNA synthesis and cloning. The screening of 3,700 clones resulted in 4 positive hybridization signals. Nucleotide sequence analysis of clones we designated pmβ N-12E4, and pmβN-8B3 added 239 nucleotides to the 3' coding and untranslated sequences. Although oligo dT primed, none of our clones contained the entire 3' untranslated region of βNGF mRNA due to incomplete synthesis of the second DNA strand or to extensive S1 nuclease treatment. Northern blot analysis (FIG. 2) indicated that the polyA sequence was not far beyond the sequences we cloned. Further details of the preparation of oligo dT primed cDNA clones from enriched mRNA are provided hereinafter.

Isolation and characterization of the human chromosomal βNGF gene.

Figure 5A:
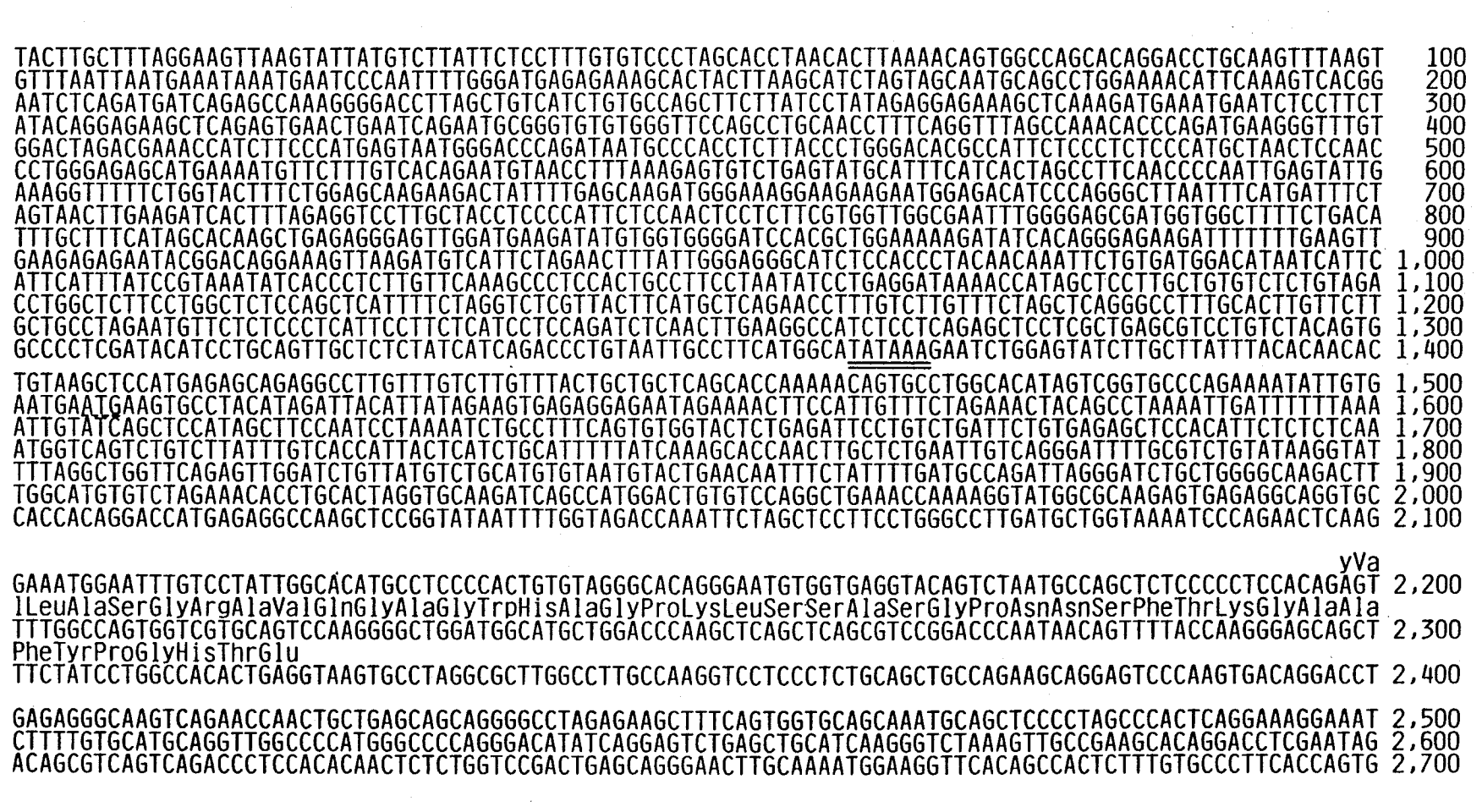
Figure 5B:
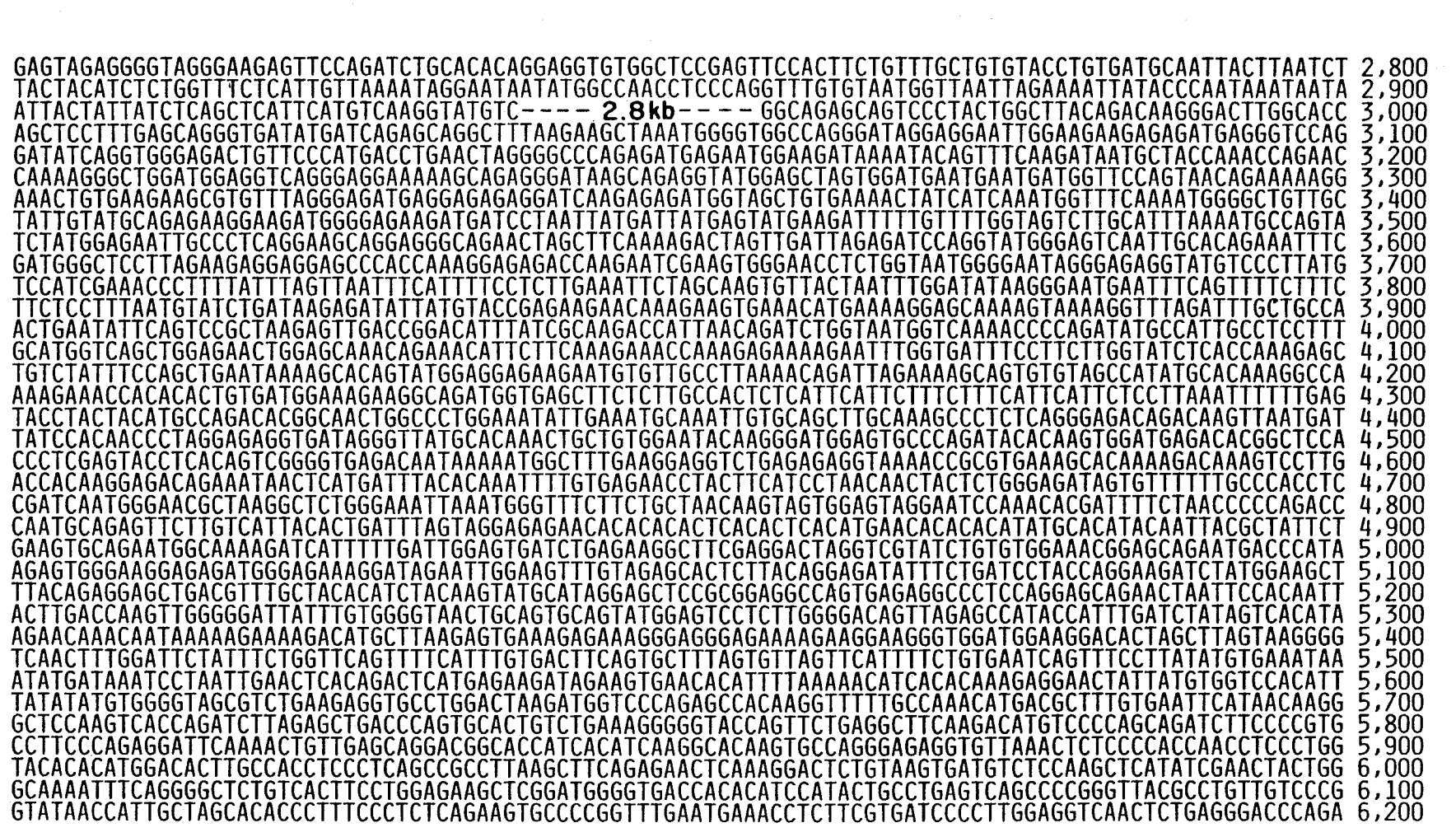
Figure 5C:
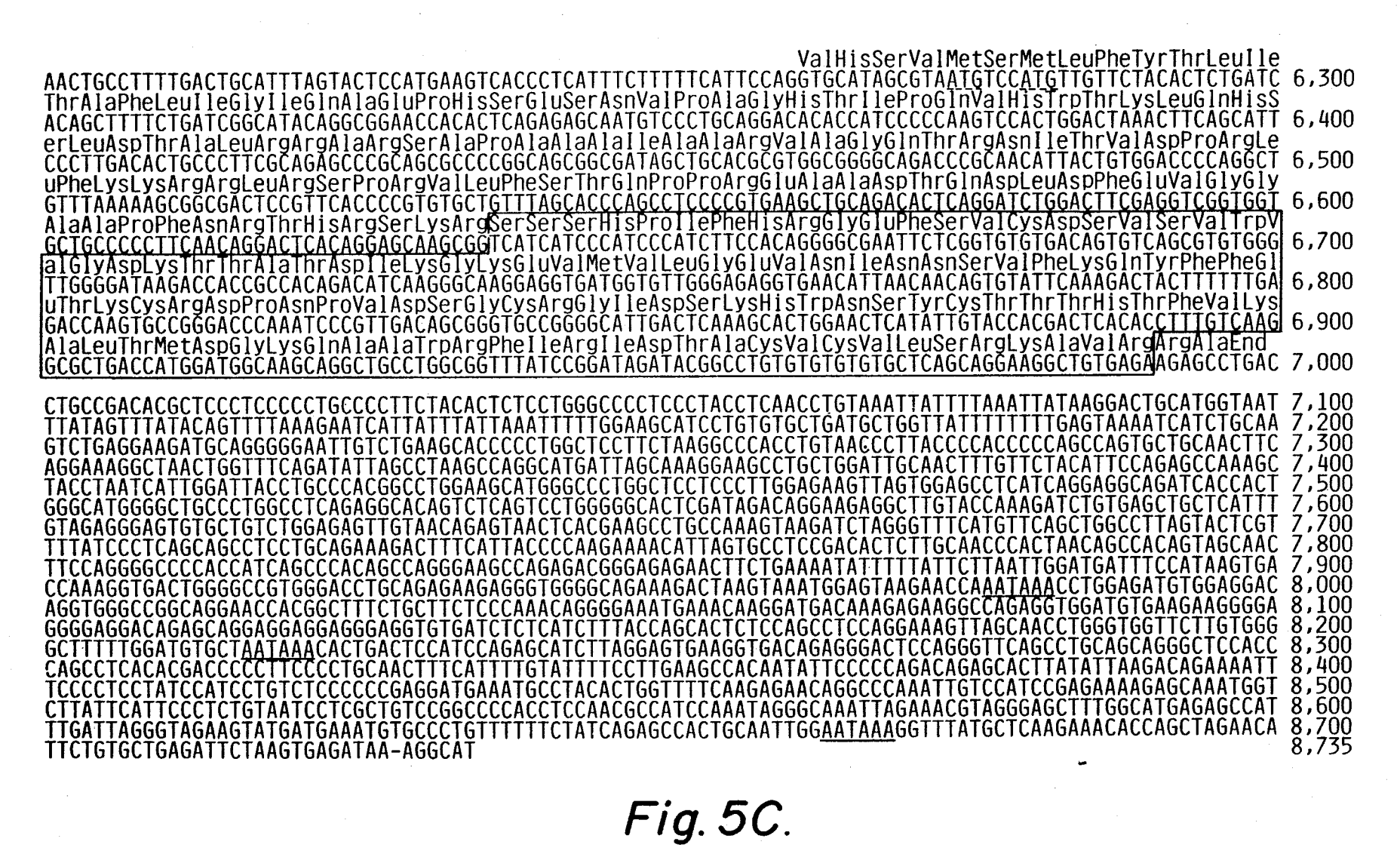

A human gene library (consisting of 15-20 kb, partial HaeIII/AluI human fetal liver DNA fragments inserted into λCharon 4A vectors) was screened using the 470 bp mouse NGF cloned cDNA fragment (pmβN-9G1 RsaI fragment) described above as radioactive hybridization probe. A total of 27 recombinant phage were plaque purified and partially characterized by EcoRI digestion; the 27 phage displayed 6 different types of restriction pattern. Each patterns category shared restriction fragments and thus appeared to overlap the same genomic region. The phage designated γhβN8 was further characterized by physical mapping and nucleotide sequencing; FIG. 4 shows a physical map of clone γhβN8 and regions flanking its sequences in the human genome, generated by phage mapping, sequencing and genomic Southern blotting experiments. A portion of a 12,000 bp nucleotide sequence derived from subcloned, overlapping EcoRI and HindIII fragments is shown in FIG. 5.

Comparison of the sequences of mouse βNGF cDNA with the human βNGF gene.

The mouse βNGF cDNA sequence contains a reading frame with the potential to code for mature βNGF, and the predicted amino acid sequence corresponds to the known sequence of mouse βNGF. Angeletti, et al, *Biochemistry*, 12: 90 (1973) and 12: 100 (1973). Unexpectedly, the cDNA sequence predicts a C-terminal, arginine-glycine dipeptide extension, linked onto the end of the reported sequence for mouse βNGF.

The human βNGF gene contains a region predicting an amino acid sequence approximately 90 percent homologous with the mature mouse βNGF amino acid sequence, which, therefore, must be the gene for human βNGF. The human βNGF protein also has a C-terminal dipeptide extension.

When one aligns the human and mouse βNGF sequences (FIG. 6) it becomes clear that extensive homology extends a significant distance upstream from the known sequence of the mature mouse protein. Evidence has been presented for the existence of a 22,000 dalton biosynthetic pro- βNGF precursor. Berger and Shooter, *Proc. Nat. Acad. Sci. (USA)*, 74: 3647, (1977), which may extend upstream from the mature protein to a potential arginine-arginine cleavage site at nucleotide positions 419 and 420 in FIG. 6. The nucleotide sequence-predicted precursor is longer than that previously detected; as will be described below, the entire prepro-β-NGF sequence is predicted to have a molecular weight of 27,000, the pro-sequence is predicted to be 25,000 daltons, and considering the presence of specific pairs of arginine residues, processing intermediates of 21,500 and 18,000 daltons exist within the cell.

Localization of the Initiation Methionine Codon and Signal Sequence.

Three methionine residues are candidates for designation as the protein synthesis initiation codon (amino acids −187, −121 and −119 in FIG. 6); however several factors strongly implicate amino acid −121 of our sequence as the actual initiation codon employed. Since βNGF is a secreted protein, the initiation codon is likely to be followed by a signal sequence for cotranslational transfer of this polypeptide into the lumen of the endoplasmic reticulum. Amino acids −121 to −104 represent an excellent candidate signal sequence. These 18 amino acids are of the correct length and include a stretch of six completely hydrophobic amino acids (ala-phe-leu-ile-gly-val). Cleavage by signal peptidase could occur between the small amino acid ala−104 and the glu residue at position −103. It is known that signal peptidase cleaves after an identical gln-ala sequence to leave an identical N-terminal glu residue in the case of pre-alpha lactalbumin. The stretch of amino acids following the met residue at position −187 contains a high percentage of polar and charged amino acids and bears no resemblance to any previously described signal sequence.

Therefore, it seems most likely that methionine −121 is used for translation initiation of mouse and human prepro-βNGF which would result in a 27,000 dalton preprohormone and a 25,000 dalton pro-βNGF if signal peptide processing occurs at residue −104.

Direct expression of human βNGF in E. coli.

EcoRI fragments from λhβN8 were subcloned in pBR322. A subclone plasmid we designated phβN8-B9 contained a 2 kb human DNA insert, including most of the sequences coding for the human βNGF subunit. Sequencing determined that only the 10 NH₂-terminal amino acids were excluded from this sequence. Our approach for expression of the βNGF coding sequence in *E. coli* was to excise the largest possible fragment from the βNGF coding portion of phβN8-B9, to subsequently fill in missing codons, and to modify the 5' and 3' ends of the sequence to make it suitable for insertion into an *E. coli* expression plasmid. The expression system employed was the Trp promoter system of pHGH207-1, H. de Boer et al., "P.N.A.S."80: 21-25 (Jan., 1983).

The plasmid phβN8-B9 was digested with EcoRI and HgiAI and a ∼300 bp fragment was isolated from the digestion mixture. This fragment is shown in FIG. 7, with the sticky end termini resulting from the two step digestion indicated. In order to construct the 5' end of the human βNGF sequence for expression, the codons for the 10 missing amino acids, the initiator methionine codon (ATG), and nucleotides preceding the ATG which are part of a ribosome binding site and include the cleavage site for the restriction endonuclease XbaI were added; four oligonucleotides were chemically synthesized for this purpose and are shown in FIG. 7 as oligonucleotides I-IV.

The 3' end of the βNGF coding region was modified as follows: the nucleotide sequence of both DNA strands downstream from the single HgiAI site shown in FIG. 7 (at amino acid position Val 111 and Leu 112 of the mature human βNGF) was chemically synthesized, including a termination codon (TAG) following Arg 118 and a SalI sticky end. These oligonucleotides are fragments V and VI in FIG. 7.

Synthetic oligonucleotides I-VI were radioactively labeled with T4 polynucleotide kinase and β-$^{32}$P-ATP, and the radioactive oligonucleotides were mixed with the ∼300 bp hβNGF DNA fragment in T4 DNA ligase buffer. Ligation was carried out with 10 units of T4 DNA ligase at 12° C. for 12 hrs. The mixture was phenol extracted and the DNA was precipitated in 70 percent ethanol. The precipitate was dried, dissolved in restriction endonuclease buffer, and the enzymes XbaI and SalI were added. Digestion was carried out for 2 hrs.

Preparative gel electrophoresis of the DNA mixture and autoradiography demonstrated the presence of a radioactive doublet at ∼370 bp. The bands were cut out separately and electrophoretically eluted. The eluted DNA fragments were then ligated (T4 DNA ligase) to a HGH-Trp expression plasmid designated pHGH207-1 that had been treated with bacterial alkaline phosphatase after digestion with XbaI and SalI. (The alkaline phosphatase treatment was used to prevent reinsertion of the HGH fragment into the Trp expression vector.) The ligation mixture was used to transform *E. coli* K12/294 (ATCC 31446). Ampicillin resistant and tetracycline sensitive colonies were selected on agar plates; two hundred colonies were screened for the presence of human βGF sequences by hybridization with a radioactive 300 bp EcoRI/HgiAI probe. Twelve positive colonies were analyzed for the presence of immunoreactive βNGF molecules in their cell extracts using rabbit anti-mouse βNGF antibodies on a Western blot. All but one clone showed a positive signal of the expected molecular weight, compared with a negative control extract. DNA sequence analysis of one of the clones verified that the final plasmid, designated by us as PhβNGFtrpl, which resulted in human βNGF expression had the originally planned construction.

Figure 8:
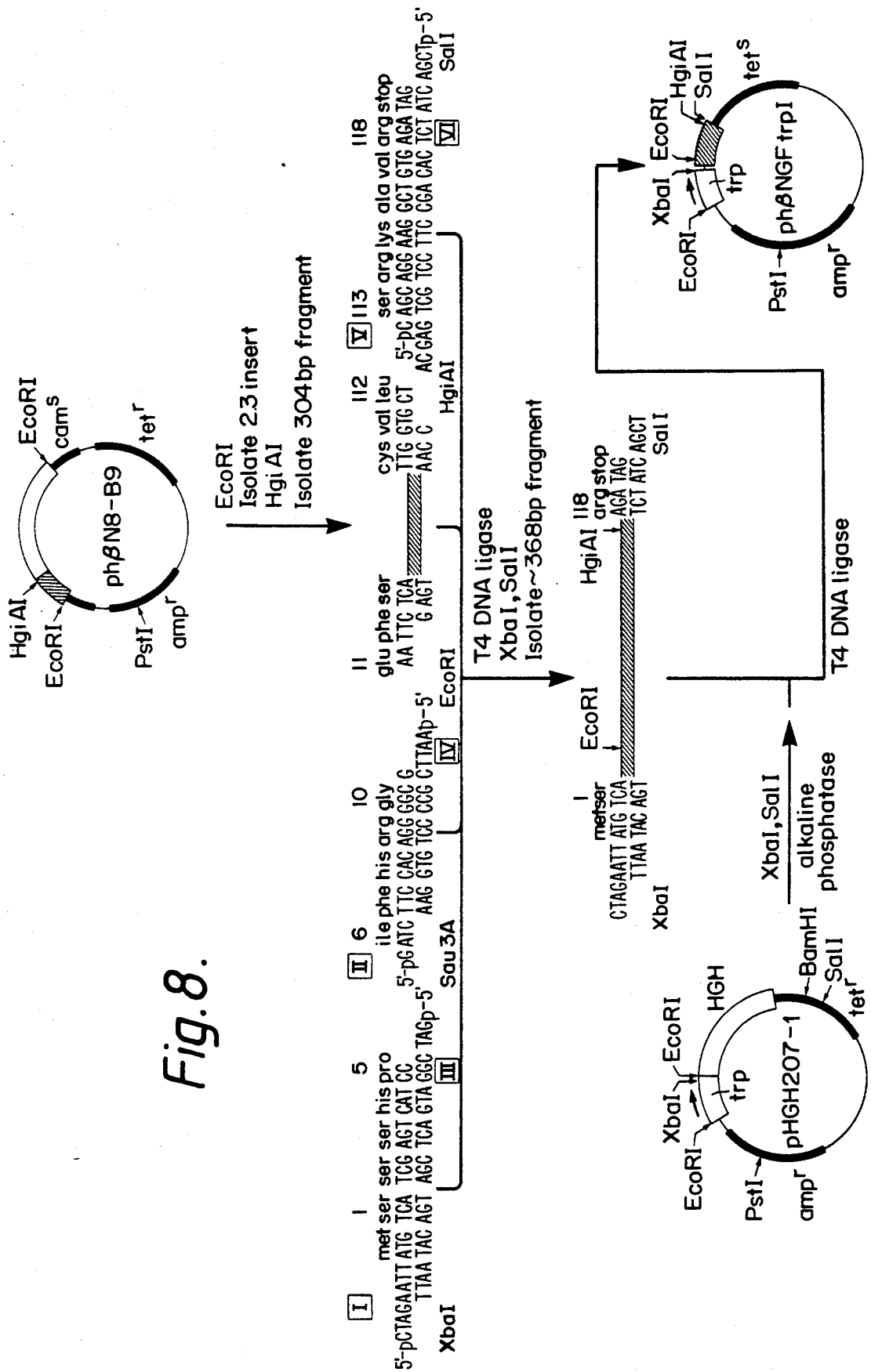
FIG. 8 depicts a portion of the process for assembling the plasmid phβNGFtrpl for transformation of *E. coli* to express human βNGF.

The sequence of operations from digestion of plasmid phβN8-B9 with EcoRI and HgiAI to assembly of plasmid phβNGFtrpl is shown in FIG. 8. The plasmid pHGH207-1 was obtained (H. de Boer et al., op cit.)

from plasmid pHGH207, by digestion with BamHI followed by partial digestion with EcoRI. The largest fragment which contained the trp promoter was isolated. The largest EcoRI-BamHI fragment from pBR322 was also isolated and the two fragments were ligated and used to transform *E. coli* K12/294 (ATCC 31446). Clones resistant to both ampicillin and tetracycline contained pHGH207-1.

Construction and identification of bacterial clones containing mNGF cDNA sequences.

Two pools of 8 primers each (14 bases) were chemically synthesized. Each primer was complementary to a potential mRNA sequence for amino acids 93–96 and a portion of 97. A mixture of the 16 oligonucleotides was used to specifically prime the synthesis of cDNA on poly(A+)RNA. 220 pmoles (1 µg) of each pool of 8 primers (440 pmoles total, 2 µg) were annealed with 40µg poly(A+) RNA in 50 µl of 100 mmole KCl by incubating for 4 minutes each at 90° C., 68° C., 42° C., and 37° C. $^{32}$P-labeled cDNA was synthesized in a 100 µl reaction in 50 mM Tris pH 8.3, 10 MM MgCl$_2$, 10 mM DTT, 50 mM KCl. The reaction contained, in addition to annealed mixture, 500 µM dATP, TTP, dGTP, 100 µM dCTP, 20 µCi [α-$^{32}$P]dCTP (2000 Ci/mmole, Amersham), 0.5 units/µl RNAsin, and 90 units reverse transcriptase. First strand synthesis was for 60 minutes at 37° C. The reaction was boiled for 3 minutes, quenched on ice for 1 minute, and spun in a microfuge. The supernatant was diluted with an equal volume ddH$_2$O and ds cDNA was synthesized with the addition of 15 units of Klenow PolI for 18 hours at 12° C. After phenol-chloroform extraction and ethanol-precipitation, the preparation was digested with 103 units of S1 nuclease in 150µl for 1 hr at 37° C. After phenol-chloroform extraction and ethanol-precipitation the cDNA was fractionated by electrophoresis on a 5 percent polyacrylamide gel. Two size ranges of cDNA were electroeluted. 132 ngm were recovered ~550 bp (upper) in length and 182 ngm were recovered 200–550 bp (lower) in length. A total of 20 ngm of each fraction was extended at the 3'-termini with 20–40 d(C) residues using terminal nucleotidyl transferase. The d(C)-tailed cDNA was annealed with 150 ngm of pBR322 which had been similarly extended with d(G) residues at the PstI site. Annealings were in 50 µl 100 mM NaCl, 10 mM Tris pH 7.5, 250 mM EDTA. Mixtures were heated to 70° C., allowed to cool slowly to 37° C. (16 hrs), then to 4° C. (6 hrs). One-half of the annealed mixture was used to transform *E. coli* K-12 strain 294. 500 colonies from each size fraction (upper and lower) were screened by filter hybridization. $^{32}$P-labeled probe was prepared from a mixture of the 16 primers (1 µg total) by phosphorylation with 200µCi [α-$^{32}$P]ATP (5000 Ci/mmole, Amersham) and polynucleotide kinase (P-L Biochemicals) by a published procedure. The filters containing the 10,000 clones were hybridized with ~1×10$^8$ cpm of the $^{32}$P-labeled probe at room temperature for 18 hours in a primer hybridization mix (100 mM Tris pH 7.5, 0.9 M NaCl, 6 mM EDTA, 1X Denhardt's solution, 100µM rATP, 1 mM NaH$_2$PO$_4$-Na pyrophosphate, 0.5 percent Nonidet P-40, 0.1 mg/ml yeast RNA (Sigma R-6750)). Filters were washed 30 minutes (3 times) in 6X SSC at 42° C. and exposed to X-ray film for 16 hrs at −70° C. with an intensifying screen (Dupont). Approximately 0.7–0.9 percent (370 upper, 460 lower) of the colonies were selected for a second round of screening with 2 additional synthetic primers which are 5' to the original priming site. 12-mers complementary to all potential mRNA sequences for amino acids 74–77 were synthesized in 2 pools of 4 primers each. Two pools of 8 14-mers each were similarly synthesized, complementary to potential mRNA sequences for amino acids 52–58 and a portion of 56. Three sets of identical filters were prepared from the "upper" and "lower" colonies selected in the first round of screening. $^{32}$P-labeled probes were prepared as before from the 4 synthetic oligonucleotides. Filters were hybridized with 0.5×10$^8$ cpm in primer hybridization mix, washed, and exposed to X-ray film. There were nine positives (3 from "lower", 6 from "upper") which hybridized with all of the 5' oligonucleotides. Plasmid DNA was isolated by a miniscreen procedure and the clone with the largest insert determined by restriction analysis. The plasmid designated pmβN-9G1 was completely sequenced by the Maxam-Gilbert method. The cDNA insert contained the 14 base primer sequence (FIG. 1, pool 1) and a total of 716 bp.

Oligo dT-primed cDNA clones prepared from mRNA enriched for µNGF message.

200 µg of poly(A+) RNA was fractionated by electrophoresis through a denaturing agarose gel composed of 2 percent agarose in 0.025 M sodium citrate pH 3.8 and 6M urea. The ribosomal bands were visualized by staining a thin vertical slice with ethidium bromide. The gel was cut into 0.5 cm slices, melted at 70° C., extracted vigorously twice with phenol and once with chloroform. After 2 ethanol precipitations the pellet was dissolved in 30 µl ddH$_2$O). 1 µl aliquots of each fraction (in 5µl 4M ammonium acetate pH 7.0) were spotted onto a dry nitrocellulose filter and screened by dot hybridization under stringent conditions. A $^{32}$P-labeled probe was prepared from the pmβN-9G1 insert by a published procedure utilizing calf thymus DNA fragments as primers in a Klenow Pol 1 reaction. The filter was hybridized with ~10$^7$ cpm in 50 mM NaPO$_4$ pH 7.0, 5X Denhardt's solution, 5X SSC, 50 µg/ml sonicated herring sperm DNA, 100µM rATP, 1 mM NaH$_2$PO$_4$-sodium pyrophosphate, and 50 percent formamide at 42° C. for 18 hrs. The filter was washed 20 minutes (3 times) in 0.2X SSC-0.1 percent SDS at 42° C. and exposed to film. Hybridization results localized the NGF message to fractions 11 and 12. Oligo dT-primed cDNA was prepared by standard methods using 10 µl each of fractions 11 and 12. The cDNA longer than 600 bp was eluted from gel slices after electrophoresis on a 5 percent polyacrylamide gel. Approximately 40 ngm cDNA from fraction 11 and 20 ngm from fraction 12 were d(C)-tailed and annealed with d(G)-tailed pBR322. About 3300 clones from fraction 11 and 1500 clones from fraction 12 were screened as colonies by filter hybridization under stringent conditions using a $^{32}$P-labeled internal HpaII fragment (216 bp) from pmβN-9G1. Filters were hybridized with 50×10$^6$ cpm at 42° C. for 18 hrs, washed, and exposed to X-ray film as before. Five clones from fraction 12 were "positive" with this probe. Restriction analyses showed they were siblings. pmβN-12E4 was completely sequenced by the Maxam-Gilbert method. Two clones from fraction 11 were "positive". The largest, pmβN-8B3, was completely sequenced by Maxam-Gilbert method.

Pharmaceutical Compositions

The human β-NGF of the present invention can be formulated according to known methods to prepare pharmaceutically useful compositions whereby the β-NGF is combined in admixture with a pharmaceutically acceptable carrier vehicle. Suitable vehicles and their formulation, inclusive of other human proteins, e.g. human serum albumin, are described for example in Remington's *Pharmaceutical Sciences* by E. W. Martin, which is hereby incorporated by reference. Such compositions will contain an effective amount of the protein hereof together with a suitable amount of vehicle in order to prepare pharmaceutically acceptable compositions suitable for effective parenteral administration to the host.

The human β-NGF hereof may be parenterally administered to subjects suffering from nerve damage or other conditions for which it is therapeutically effective. Dosage and dose rate may parallel that currently in use in clinical investigations of such agents derived, for example, from mouse salivary glands.

Notwithstanding that reference has been made to particular preferred embodiments, it will be further understood that the present invention is not to be construed as limited to such, rather to the lawful scope of the appended claims.

We claim:

1. A process which comprises transforming an *E. Coli* host cell with a replicable expression vector capable, in the host cell transformed with the vector, of expressing an isolated first DNA sequence which encodes a polypeptide comprising the human mature βNGF amino acid sequence

```
ser ser ser his pro ile phe his arg gly glu phe ser val cys
asp ser val ser val trp val gly asp lys thr thr ala thr asp
ile lys gly lys glu val met val leu gly glu val asn ile asn
asn ser val phe lys gln tyr phe phe glu thr lys cys arg asp
pro asn pro val asp ser gly cys arg gly ile asp ser lys his
trp asn ser tyr cys thr thr thr his thr phe val lys ala leu
thr met asp gly lys gln ala ala trp arg phe ile arg ile asp
thr ala cys val cys val leu ser arg lys ala val arg
``` operably linked with a second DNA sequence capable of effecting expression of the first DNA sequence in the host cell transformed with the operably linked DNA sequences.

2. An isolated DNA sequence which encodes a polypeptide comprising the human mature βNGF amino acid sequence

```
ser ser ser his pro ile phe his arg gly glu phe ser val cys
asp ser val ser val trp val gly asp lys thr thr ala thr asp
ile lys gly lys glu val met val leu gly glu val asn ile asn
asn ser val phe lys gln tyr phe phe glu thr lys cys arg asp
pro asn pro val asp ser gly cys arg gly ile asp ser lys his
trp asn ser tyr cys thr thr thr his thr phe val lys ala leu
thr met asp gly lys gln ala ala trp arg phe ile arg ile asp
thr ala cys val cys val leu ser arg lys ala val arg.
```

3. A replicable expression vector capable, in a host cell transformed with the vector, of expressing the DNA sequence of claim 2.

4. The vector of claim 3 comprising a signal sequence for the human βNGF.

5. A host cell transformed with a replicable expression vector capable of expressing in the host cell the DNA sequence of claim 2.

6. The host cell of claim 5 that is eukaryotic.

7. A host cell according to claim 6 that is a Chinese hamster ovary cell line.

8. A host cell according to claim 5 which is an *E. coli* strain.

9. The DNA sequence of claim 2 that further comprises a signal sequence for the human βNGF.

10. A host cell according to claim 5 which is prokaryotic.

11. A host cell according to claim 5 which is a mammalian cell.

12. A host cell according to claim 5 which is a yeast cell.

13. Plasmid phβNGFtrpl.

14. A host cell transformed with the plasmid of claim 13.

15. A host cell according to claim 14 which is a strain of *E. coli*.

16. A replicable vector comprising an isolated nucleic acid encoding the human pro βNGF pro sequence

```
glu pro his ser glu ser asn val pro ala gly his thr ile pro
gln val his trp thr lys leu gln his ser leu asp thr ala leu
arg arg ala arg ser ala pro ala ala ala ile ala ala arg val
ala gly gln thr arg asn ile thr val asp pro arg leu phe.
```

17. An isolated first DNA sequence which encodes a polypeptide comprising the human mature βNGF amino acid sequence

```
ser ser ser his pro ile phe his arg gly glu phe ser val cys
asp ser val ser val trp val gly asp lys thr thr ala thr asp
ile lys gly lys glu val met val leu gly glu val asn ile asn
asn ser val phe lys gln tyr phe phe glu thr lys cys arg asp
pro asn pro val asp ser gly cys arg gly ile asp ser lys his
trp asn ser tyr cys thr thr thr his thr phe val lys ala leu
thr met asp gly lys gln ala ala trp arg phe ile arg ile asp
thr ala cys val cys val leu ser arg lys ala val arg
``` operably linked with a second DNA sequence capable of effecting expression of the first DNA sequence in a host cell transformed with the operably linked DNA sequences.

* * * * *